(12) United States Patent
Kawaguchi

(10) Patent No.: US 7,713,692 B2
(45) Date of Patent: May 11, 2010

(54) NUCLEIC-ACID PROBE SUBSTRATE, SYSTEM FOR TEMPERATURE CONTROL OF THE SUBSTRATE, AND GENE DETECTION METHOD MAKING USE OF THE SAME

(75) Inventor: Masahiro Kawaguchi, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 513 days.

(21) Appl. No.: 10/602,464

(22) Filed: Jun. 23, 2003

(65) Prior Publication Data
US 2004/0009525 A1  Jan. 15, 2004

(30) Foreign Application Priority Data
Jun. 24, 2002  (JP)  ............... 2002-183247

(51) Int. Cl.
*C12Q 1/68* (2006.01)
*C12P 19/34* (2006.01)
*C12N 1/36* (2006.01)

(52) U.S. Cl. .............. 435/6; 435/91.2; 435/283.1; 435/287.2; 536/23.1

(58) Field of Classification Search ............... None
See application file for complete search history.

(56) References Cited

U.S. PATENT DOCUMENTS

| | | | | |
|---|---|---|---|---|
| 5,146,981 A * | 9/1992 | Samarov | ............... | 165/185 |
| 5,364,790 A * | 11/1994 | Atwood et al. | ............ | 435/287.2 |
| 5,587,128 A * | 12/1996 | Wilding et al. | ................ | 422/50 |
| 6,093,370 A * | 7/2000 | Yasuda et al. | .............. | 422/68.1 |
| 6,130,279 A * | 10/2000 | Suzuki et al. | ............... | 524/401 |
| 6,346,383 B1 * | 2/2002 | Kajiyama et al. | ............... | 435/6 |
| 6,657,169 B2 * | 12/2003 | Brown | ......................... | 219/476 |
| 2002/0039728 A1 * | 4/2002 | Kain et al. | ..................... | 435/6 |
| 2003/0072685 A1 * | 4/2003 | Goldman et al. | ............ | 422/102 |

FOREIGN PATENT DOCUMENTS

WO    WO 00/96561    * 11/2000

OTHER PUBLICATIONS

St. George "PCR: Running Hot and Fast" Statistical Software Supplement, Science, Feb. 27, 1997, pp. 1-13.*
labtrade.com, DNA Engine: Peltier Thermal Chcler (PTC-200).*

* cited by examiner

*Primary Examiner*—B J Forman
(74) *Attorney, Agent, or Firm*—Canon U.S.A., Inc., IP Division

(57) ABSTRACT

A system used to detect and assay genes by using a nucleic-acid probe substrate is disclosed, which can be used in highly general-purpose genetic chips usable for various purposes, and has a temperature control means enabling control of temperature of the whole genetic chip in a high reproducibility and uniformity, and further even satisfies low-cost performance. A method for detecting and assaying gene nucleic acids by using such a system is also disclosed. A heat-conductive material made up using a material having good thermal conductivity, having a shape having general-purpose properties, is used as the temperature control means, and is disposed in such a form that it covers substantially the whole substrate face or stands in contact therewith, on the back of the substrate, or on the side facing the surface to which the detecting single-stranded nucleic acid fragments have been immobilized. This makes it possible to improve the diffusion of heat in the in-plane direction of the whole substrate face. In addition, heat is given and received through such a heat-conductive material.

13 Claims, 3 Drawing Sheets

SEQUENCE LISTING

```
<160> NUMBER OF SEQ ID NOS: 3

<210> SEQ ID NO 1
<211> LENGTH: 18
<212> TYPE: DNA
<213> ORGANISM: Artificial Sequence
<220> FEATURE:
<223> OTHER INFORMATION: Synthesized DNA probe

<400> SEQUENCE: 1
actggccgtc gttttaca                                               18

<210> SEQ ID NO 2
<211> LENGTH: 18
<212> TYPE: DNA
<213> ORGANISM: Artificial Sequence
<220> FEATURE:
<223> OTHER INFORMATION: Synthesized DNA probe

<400> SEQUENCE: 2
actggccatc gttttaca                                               18

<210> SEQ ID NO 3
<211> LENGTH: 18
<212> TYPE: DNA
<213> ORGANISM: Artificial Sequence
<220> FEATURE:
<223> OTHER INFORMATION: Synthesized DNA probe

<400> SEQUENCE: 3
actggcaatc gttttaca                                               18
```

NUCLEIC-ACID PROBE SUBSTRATE, SYSTEM FOR TEMPERATURE CONTROL OF THE SUBSTRATE, AND GENE DETECTION METHOD MAKING USE OF THE SAME

BACKGROUND OF THE INVENTION

1. Field of the Invention

This invention relates to a system used to detect and assay genes, making use of a probe substrate, in particular, a nucleic-acid probe substrate. More particularly, this invention relates to a system having, when gene DNA is detected and assayed by hybridization, the function to achieve contact of a specimen with each nucleic-acid probe under the desired temperature conditions, in respect to a substrate onto which plural kinds of single-stranded nucleic acids have been immobilized in an array as nucleic-acid probes, and a method of detecting and assaying gene nucleic acids by using this system.

2. Related Background Art

As progress of methods for detecting and assaying gene DNA according to hybridization, researches relating to genetic chips (DNA chips, microarrays) are being rapidly advanced which have a use to make a plurality of detection tests simultaneously on gene DNA contained in a specimen, by immobilizing a plurality of nucleic-acid probes on a substrate. Such methods for detecting and assaying gene DNA contained in a specimen, utilizing genetic chips (DNA chips, microarrays) are expected to be applicable to various fields such as molecular biological researches and diagnoses on genetic diseases and infectious diseases.

The basic form of a genetic chip is that, in order to detect a target gene DNA according to hybridization, plural kinds of single-stranded nucleic acids having a complementary base sequence in respect to the base sequence of the target genes have been immobilized in an array on the surface of a substrate made of glass or the like. As the fragments of single-stranded nucleic acids having a complementary base sequence in respect to the base sequence of the target genes, which are utilized as hybridization probes, DNA oligomers called oligo DNA which are synthesized by a chemical route or complementary-stranded DNA fragments called cDNA which are biosynthesized by an enzymatic route using as a template any genes derived from biological tissues are commonly utilized. With regard to the immobilization of fragments of single-stranded nucleic acids to the substrate surface, it is, in the case of the oligo DNA, roughly classified into i) a method in which, like the method disclosed in, e.g., U.S. Pat. No. 5,474,796 (or Japanese Patent Application Laid-Open No. 9-500568; applicant: ProtoGene Laboratories), terminals are previously immobilized and then DNA molecules themselves are one by one synthesized on the substrate to form immobilized nucleic-acid fragments, and ii) a method in which, like the method disclosed in, e.g., Japanese Patent Application Laid-Open No. 11-187900 (applicant: CANON KABUSHIKI KAISHA), oligo DNA is separately synthesized and thereafter nucleic-acid fragments are immobilized to the substrate surface by various binding means.

As means for immobilizing to the substrate surface the nucleic-acid fragments prepared separately, various methods are proposed as exemplified by adsorption immobilization which utilizes electric charges the substrate has and electric charges the nucleic-acid fragments have, and immobilization in which the substrate surface is coated with poly-L-lysine or an aminosilane coupling agent and the resulting coating film is utilized so as to improve immobilization efficiency.

Meanwhile, in cross-hybridization (hybridization reaction) on nucleic-acid probes having been immobilized to the substrate surface, gene DNA contained in a specimen solution is single-stranded and then bound to portions which are complementary to the base sequence of the nucleic-acid probes to form a double-stranded structure. Accordingly, the nucleic-acid probes and the specimen solution must be heated to a stated temperature. In addition, gene DNA not having any complementary base sequence in respect to the base sequence of the nucleic-acid probes but having a similar base sequence also causes, in some cases, pseudo-cross-hybridization (mismatch hybridization reaction) to form gentle bonds to the nucleic-acid probes. Furthermore, unreacted adulterant DNA having no similarity in base sequence may also adhere to the substrate surface by physical adsorption or the like. In order to selectively remove such unnecessary DNA molecules standing bound weakly, they are heated to a temperature at which any redissociation of gene DNA having achieved the intended hybridization reaction does not take place but the detachment of the unnecessary DNA molecules standing bound weakly proceeds, and then washed to remove them.

In detection operation making use of the genetic chip, in order to detect only the target gene DNA in a high reproducibility, it is particularly necessary to control in a high precision the heating temperature in the step of hybridization reaction of the target genes in a specimen with the nucleic acids (probes) having been immobilized on the genetic chip, and the heating temperature in the step of washing to selectively remove the similar genes having caused mismatch hybridization reaction and the unreacted adulterants. Also, commonly, any temperature variations between the respective steps have a great influence on the reproducibility of detection results.

Some means are proposed by which the detection precision and reproducibility is kept from lowering because of such temperature variations between the respective steps. For example, a polynucleotide detection chip and a polynucleotide detection system which are disclosed in Japanese Patent Application Laid-Open No. 2000-342264 employs a method in which sections are set for each kind of nucleic-acid fragments (probes) having a sequence which is complementary to the target genes contained in a specimen, and a micro-heater is provided for each section of a detecting chip so that proper temperature control can be made. In this method, the system has so greatly complicate construction that the detecting chip exclusively used therefor and also the whole detection system can not help being expensive. In addition, inasmuch as the micro heater is provided for each section, it is also difficult to make the whole system compact.

In a hybridization reaction detection method and detection system disclosed in Japanese Patent Application Laid-Open No. 2001-255328, changes with time in the course of reaction are pursued so that any influence of temperature changes of an array formed on a glass substrate can be eliminated to aim at highly precise detection. In this method, however, one-sheet array must continuously be pursued and examined using an instrument such as a microscope while the reaction is carried out, and hence it is difficult to examine a large number of arrays on substrates.

Genetic chips packaged in original shapes are also commercially available, as typified by GeneChip (available from Affymetrix Co.). These commercially available genetic chips are genetic chips supposing detection operation which utilizes a corresponding system exclusively used therefor, and hence have poor general-purpose properties. In addition, not only the system of exclusive use but also the genetic chips themselves are very expensive.

Meanwhile, in uses for researches as in universities and so forth, a genetic chip formed by immobilizing original and various detecting nucleic-acid fragments must be produced. Accordingly, a method is commonly used in which, using an array manufacturing system called a pin spotter, nucleic-acid fragments are immobilized on a slide glass substrate surface-treated with poly-L-lysine or the like. The genetic chip produced on such a general-purpose slide glass substrate, produced by this method, looks a simple glass plate in appearance. Of course, nothing is devised at all for temperature control.

Thus, it is sought to develop a detection system which can be used also when, e.g., the genetic chip is used which is formed on a general-purpose slide glass substrate, utilized in the uses for researches, has a temperature control means enabling control of temperature of the whole genetic chip in a high reproducibility and uniformity, and also has low-cost performance and high general-purpose properties as a whole.

SUMMARY OF THE INVENTION

Accordingly, an object of the present invention is to provide a system used to detect and assay genes by using a nucleic-acid probe substrate, which can be used in highly general-purpose genetic chips usable for various purposes, and in addition has a temperature control means enabling control of temperature of the whole genetic chip in a high reproducibility and uniformity, and further even satisfies low-cost performance, and to provide a method for detecting and assaying gene nucleic acids by using such a system.

The present inventor has put extensive studies forward so as to solve the above problems. As the result, he has discovered that slide glass substrate itself used in producing the genetic chip has not necessarily high thermal conductivity in order to control the temperature of the whole genetic chip in a high reproducibility and uniformity, and for that reason may also cause local non-uniformity of temperature distribution. Based on this finding, the present inventor has made further studies. As the result, he has discovered that a heat-conductive material may be disposed in contact with the back of the slide glass substrate to make the heat diffuse effectively in the in-plane direction through such a heat-conductive material, and also this heat-conductive material may be brought into direct contact with a heating means or cooling means to control the temperature of the heat-conductive material itself, whereby the whole slide glass substrate disposed in contact can also be kept at the desired temperature without any temperature non-uniformity and also in a high precision. Thus, he has accomplished the present invention.

That is, the present invention provides a system for temperature control of a nucleic-acid probe substrate. According to a first embodiment of the system for temperature control of a nucleic-acid probe substrate according to the present invention, it is a system for temperature control of a nucleic-acid probe substrate, which controls the temperature of a substrate to the substrate surface of which a plurality of nucleic-acid probes containing single-stranded nucleic acid fragments having a complementary sequence in respect to a target DNA have been immobilized in order that the target DNA contained in a specimen is detected according to hybridization; the system being characterized by having:

a heat conduction means formed of a heat-conductive material disposed on the back of the substrate to the substrate surface of which the plurality of single-stranded nucleic acid fragments have been immobilized, and in contact with the back of the substrate;

a heating means or cooling means which is provided in contact with the heat-conductive material; and a means for controlling the amount of heat flowing across the heating means or cooling means and the heat-conductive material, to control the temperature of the heat-conductive material;

the temperature of the substrate disposed in contact being controlled through the temperature control of the heat-conductive material.

According to a second embodiment of the system for temperature control of a nucleic-acid probe substrate according to the present invention, it is a system for temperature control of a nucleic-acid probe substrate, which controls the temperature of a substrate to the substrate surface of which a plurality of nucleic-acid probes containing single-stranded nucleic acid fragments having a complementary sequence in respect to a target DNA have been immobilized in order that the target DNA contained in a specimen is detected according to hybridization; the system being characterized by having:

a heat conduction means formed of a heat-conductive material disposed on the surface of the substrate to the substrate surface of which the plurality of single-stranded nucleic acid fragments have been immobilized, facing, and in contact with, the substrate surface, partly leaving a space for feeding the specimen thereinto;

a heating means or cooling means which is provided in contact with the heat-conductive material; and a means for controlling the amount of heat flowing across the heating means or cooling means and the heat-conductive material, to control the temperature of the heat-conductive material;

the specimen fed into the space and the substrate surface, which are in contact with the heat-conductive material, being temperature-controlled through the temperature control of the heat-conductive material.

In the above second-embodiment system, the heat-conductive material may preferably be formed of any one of a metal and a resin or a composite of these two kinds or more.

The present invention also provides a method of detecting genes by using a means for temperature control of such an nucleic-acid probe substrate. That is, according to a first embodiment of the gene detection method according to the present invention, it is a method for detecting genes by utilizing as a detection means a substrate to the substrate surface of which a plurality of nucleic-acid probes containing single-stranded nucleic acid fragments having a complementary sequence in respect to a target DNA have been immobilized in order that the target DNA contained in a specimen is detected according to hybridization; the method being characterized by:

disposing a heat-conductive material on the back of the substrate to the substrate surface of which the plurality of single-stranded nucleic acid fragments have been immobilized, and in contact with the back of the substrate;

disposing a heating means or cooling means in contact with the heat-conductive material; and providing a means for controlling the amount of heat flowing across the heating means or cooling means and the heat-conductive material, to control the temperature of the heat-conductive material;

the detection being operated while the substrate standing bonded sandwichedly and the specimen standing in contact with the substrate surface are temperature-controlled through the temperature control of the heat-conductive material.

The above method may be a method in which, in a plurality of steps involved in the gene detection operation, the substrate and the specimen standing in contact with the substrate surface are temperature-controlled; and the temperature in the plurality of steps requiring temperature control is successively controlled by the temperature control means which utilizes the heating means.

The above method may also be a method in which, in a plurality of steps involved in the gene detection operation, the substrate and the specimen standing in contact with the substrate surface are temperature-controlled; and the temperature in the plurality of steps requiring temperature control is successively controlled by the temperature control means which utilizes the cooling means.

In the above method, as the heat-conductive material, which is utilized for the temperature control of the specimen standing in contact with the substrate surface, a heat-conductive material may preferably be used which is formed of any one of a metal and a resin or a composite of these two kinds or more.

In addition, according to a second embodiment of the gene detection method according to the present invention, it is a method for detecting genes by utilizing as a detection means a substrate to the substrate surface of which a plurality of nucleic-acid probes containing single-stranded nucleic acid fragments having a complementary sequence in respect to a target DNA have been immobilized in order that the target DNA contained in a specimen is detected according to hybridization; the method being characterized by:

disposing a heat-conductive material on the surface of the substrate to the substrate surface of which the plurality of single-stranded nucleic acid fragments have been immobilized, facing, and in contact with, the substrate surface, partly leaving a space for feeding the specimen thereinto;

disposing a heating means or cooling means in contact with the heat-conductive material; and providing a temperature control means for controlling the amount of heat flowing across the heating means or cooling means and the heat-conductive material, to control the temperature of the heat-conductive material;

the detection being operated while the specimen fed into the space and the substrate surface, which are in contact with the heat-conductive material, being temperature-controlled through the temperature control of the heat-conductive material by the temperature control means during the operation of gene detection.

The above second-embodiment method may be a method in which, in a plurality of steps involved in the gene detection operation, the substrate and the specimen standing in contact with the substrate surface are temperature-controlled; and the temperature in the plurality of steps requiring temperature control is successively controlled by the temperature control means which utilizes the heating means.

The above second-embodiment method may also be a method in which, in a plurality of steps involved in the gene detection operation, the substrate and the specimen standing in contact with the substrate surface are temperature-controlled; and the temperature in the plurality of steps requiring temperature control is successively controlled by the temperature control means which utilizes the cooling means.

In the above second-embodiment method, as the heat-conductive material, which is utilized for the temperature control of the specimen standing in contact with the substrate surface, a heat-conductive material may preferably be used which is formed of any one of a metal and a resin or a composite of these two kinds or more.

In the present invention, in operating the gene detection by using a genetic chip, the heat-conductive material made up using a material having good thermal conductivity, having a shape having general-purpose properties, is used as a means for controlling the temperature of the genetic chip, and is disposed in such a form that it covers substantially the whole substrate face or stands in contact therewith, on the back of the substrate, or on the side facing the surface to which the detecting single-stranded nucleic acid fragments have been immobilized. This makes it possible to improve the diffusion of heat in the in-plane direction of the whole substrate face. In addition, a temperature control means which gives and receives heat through such a heat-conductive material is used. This makes it possible to control the temperature of the whole genetic chip to the desired temperature in a good efficiency and a good reproducibility. Such a temperature control means can be made up using inexpensive members and devices, and can simply be modified in accordance with the shape of the substrate used for the genetic chip. Thus, high general-purpose properties can be provided, and also, utilizing this temperature control means, the temperature inside the genetic chip can also be kept from scattering in the operation of gene detection to achieve improvements in precision and reproducibility of the assay itself.

The present invention still also provides a probe substrate and a system for temperature control of the probe substrate.

The probe substrate according to the present invention is characterized by having a substrate, a plurality of probes bindable specifically to a target substance which have been immobilized to the substrate surface, and a heat-conductive material for controlling the temperature of the substrate; the material being disposed in contact with the back of the substrate.

The system for temperature control of a probe substrate according to the present invention is a probe substrate temperature control system for controlling the temperature of a probe substrate to the substrate surface of which a plurality of probes bindable specifically to a target substance have been immobilized in order to detect the target substance; the system being characterized by having:

a heat conduction means comprising a heat-conductive material disposed on the side opposite to the surface of the probe substrate to which surface the detecting target substance have been immobilized, and in contact with the back of the substrate;

a heating means or cooling means which is provided in contact with the heat-conductive material; and a means for controlling the amount of heat flowing across the heating means or cooling means and the heat-conductive material, to control the temperature of the heat-conductive material;

the temperature of the substrate disposed in contact being controlled through the temperature control of the heat-conductive material.

The present invention still also provides another probe substrate and another system for temperature control of the probe substrate.

The probe substrate according to the present invention is characterized by having a substrate, a plurality of probes bindable specifically to a target substance which have been immobilized to the substrate surface, and a heat-conductive material for controlling the temperature of the substrate; the material being disposed on the surface of the substrate to the substrate surface of which the plurality of probes have been immobilized, facing, and in contact with, the substrate surface, partly leaving a space for feeding the specimen thereinto.

The system for temperature control of a probe substrate according to the present invention is a probe substrate temperature control system for controlling the temperature of a probe substrate to the substrate surface of which a plurality of probes bindable specifically to a target substance have been immobilized in order to detect the target substance; the system being characterized by having:

a heat conduction means comprising a heat-conductive material disposed on the surface of the substrate to the substrate surface of which the plurality of probes have been immobilized, facing, and in contact with, the substrate surface, partly leaving a space for feeding the specimen thereinto;

a heating means or cooling means which is provided in contact with the heat-conductive material; and a means for controlling the amount of heat flowing across the heating means or cooling means and the heat-conductive material to control the temperature of the heat-conductive material;

the temperature of the substrate disposed in contact being controlled through the temperature control of the heat-conductive material.

DESCRIPTION OF THE PREFERRED EMBODIMENTS

Figure 1:
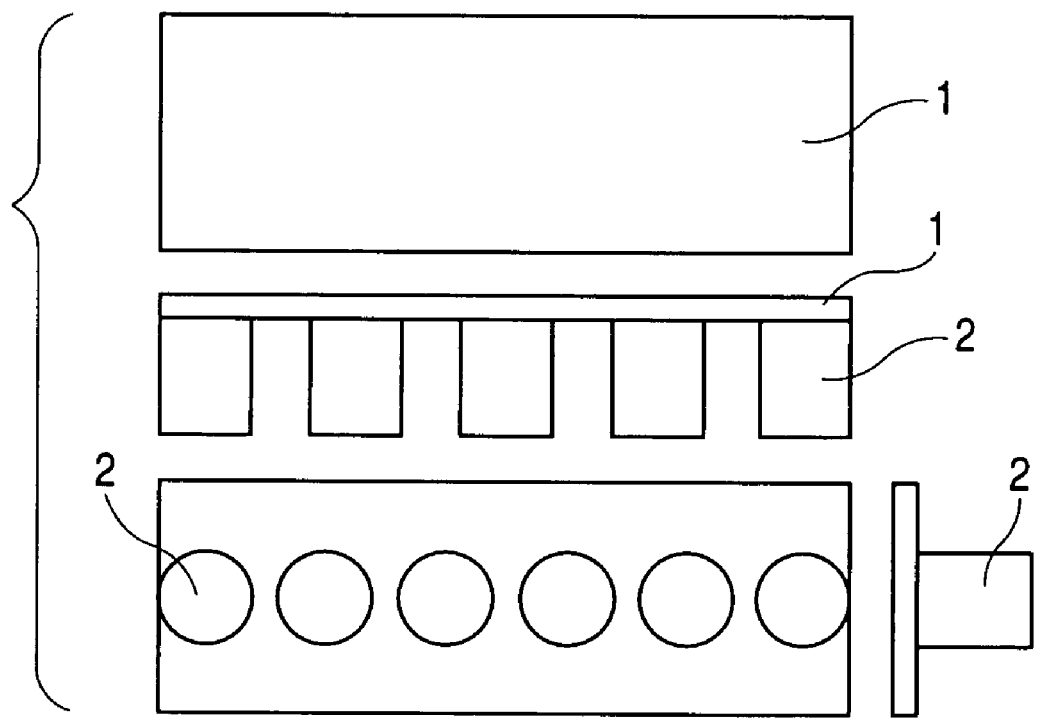
FIG. 1 is a diagrammatic illustration of an embodiment of a heat conduction unit used in the temperature control system according to the present invention.

The present invention is described below in detail.

To give characteristic points of the present invention specifically, when the whole substrate onto which single-stranded nucleic acid fragments having a complementary base sequence in respect to a target gene DNA have been immobilized in order to detect the target gene DNA contained in a specimen is controlled to the desired temperature, the heat-conductive material made up using a material having good thermal conductivity is disposed in such a form that it covers substantially the whole substrate face or stands in contact therewith, on the back of the substrate, or on the side facing the surface to which the detecting single-stranded nucleic acid fragments have been immobilized, whereby the diffusion of heat in the in-plane direction of the whole substrate face can be improved. In addition, a temperature control means which gives and receives heat through a heat conduction means constituted of such a heat-conductive material can be provided.

The heat-conductive material used as the heat conduction means may be disposed in contact with the back or so of the substrate before the step of immobilizing the detecting single-stranded nucleic acid fragments, unless this does not hinder the step of producing the nucleic-acid probe substrate, in particular, the step of immobilizing the detecting single-stranded nucleic acid fragments to the substrate surface. Also, in disposing the heat-conductive material in contact, a means of permanent bonding or the like may be used, or it may be detachably constructed, without any problems. However, the heat-conductive material must be in such a form that it can sufficiently achieve, over the whole substrate surface, close thermal contact with and adhesion to the slide glass substrate used in the nucleic-acid probe substrate. To show an example of methods by which it is disposed in contact, a method may be exemplified in which a pressure-sensitive paste is applied in a small quantity between the substrate onto which the detecting single-stranded nucleic acid fragments (hereinafter often "probes") have been immobilized (hereinafter often "genetic chip") and the heat-conductive material, and the pressure-sensitive adhesion of the paste thin-coating layer thus formed is utilized so that the heat-conductive material can be disposed in close contact with the genetic chip.

Here, as this pressure-sensitive paste, a material may be selected which does not cause any hardening, drying or the like as the genetic chip is heated or cooled (temperature-controlled) during the operation of gene detection. Also, the paste thin-coating layer may preferably be formed in a layer thickness as small as possible within the range that it can exhibit the pressure-sensitive adhesion. More specifically, it should be minded that the paste is used in a quantity as small as possible so that it does not interfere with the heat conduction across the heat-conductive material and the back or so of the substrate. If the paste itself to be used is endowed with a sufficient thermal conductivity comparable to that of the heat-conductive material, the layer thickness of the paste thin-coating layer may be set within a range of larger thickness although it is preferable to make the thickness as small as possible.

As materials for the heat conduction means used as the heat-conductive material, they may include metals and resins. Stated more specifically, they are materials having a higher thermal conductivity than the slide glass used as the substrate in the present invention. As usable metals, they may include iron, aluminum, copper, brass and stainless steel. Such a good heat-conductive material making use of any of these metals may be used as a block-like or plate-like mass. Also usable are those formed to exhibit uniform thermal conductivity, by, e.g., sintering a flaky finely divided material.

As to resin materials usable as the heat conduction means heat-conductive material, there are no particular limitations. Those capable of exhibiting higher thermal conductivity are more preferred. For example, a resin may preferably be mixed with a powdery metal to reinforce heat conduction performance.

The heat conduction means constituted of the heat-conductive material may preferably be so shaped that, in the case of a solid form, it can have good contact at its flat face portion of course, disposed in contact with the back or so of the substrate, and after the shape of a heating means or cooling means disposed in contact with this heat conduction means. That is, it may preferably be so shaped that the heat conducted to the substrate may uniformly be conducted to the region where the probes of the genetic chip in which the nucleic-acid probes stand immobilized to the substrate surface are fixed. The heat conduction means is also not necessarily required to be used in a solid state. For example, it may also be used in a state having flowability, such as a pasty form or a gummy form.

Typical embodiments of the present invention are described in detail with reference to the drawings.

Figure 2:
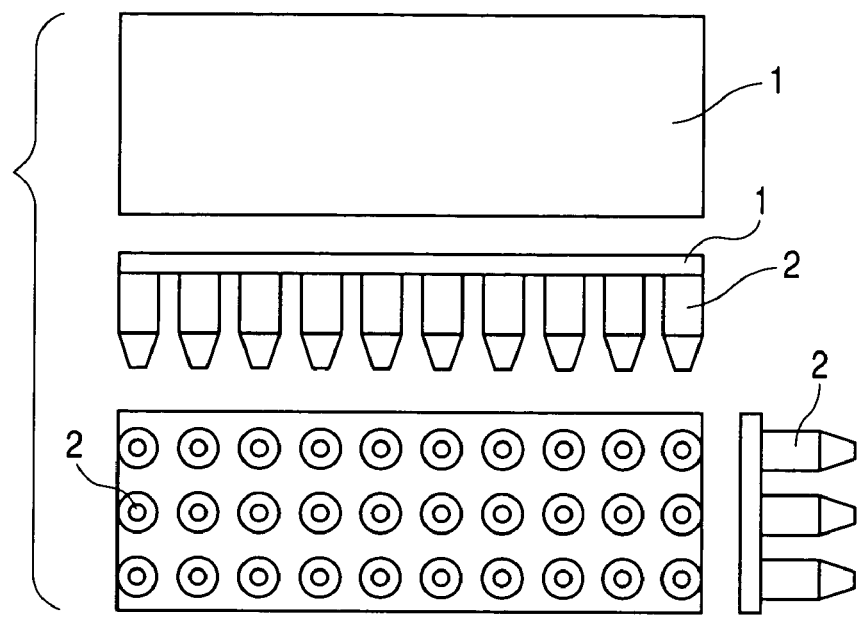
FIG. 2 is a diagrammatic illustration of another embodiment of a heat conduction unit used in the temperature control system according to the present invention.

FIG. 1 shows an example of a heat conduction unit made of a metal, which is used in the present invention and has the heat conduction means described above. FIG. 2 also shows another example. In the heat conduction units shown in FIGS. 1 and 2, a genetic chip (not shown) is disposed on a genetic-chip sandwiching bond face 1 having a flat surface, in such a way that the back of the former's substrate is in contact with the latter. Meanwhile, legs 2 provided on the opposite side of the sandwiching bond face 1 are formed of the heat conduction means heat-conductive material, and have been shaped after the shape of a temperature control means (not shown) serving as a heating means or cooling means. Utilizing such legs 2, the heat conduction unit is set to the temperature control means. In these examples, a heat block device or a programmable heat block device for PCR (polymerase chain reaction) is used as the temperature control means. Here, the shape of each heat conduction unit is diagrammatically shown assuming that the heat conduction unit is set to such a heat block. More specifically, the legs 2 shown in FIGS. 1 and 2 are so arranged and formed that they can be inserted to the holes of the heat blocks; the holes being used to insert microtubes thereinto.

In order to enhance the thermal conductivity of heat conduction across the temperature control means (heating means or cooling means) and the heat conduction unit, the legs 2 may preferably be in such a size that they can closely be fit to the inserting holes of the heat block. Incidentally, their shape must be designed taking account of the coefficient of thermal expansion of the heat block and also the coefficient of thermal expansion the metallic material constituting the heat conduction unit exemplified above exhibits. Taking account of these, an oil or the like may also be used in order to fill up any gaps between the legs 2 and the inserting holes of the heat block to complement the thermal conductivity.

As a material for the heat conduction unit, aluminum may preferably be used because it is relatively light-weight and has superior workability. The heat conduction unit having the shape shown in FIGS. 1 and 2 each may also be prepared with a resin. The resin, however, has commonly a disadvantage that it has a thermal conductivity inferior to that of the metallic material and consequently the genetic chip may have a slower temperature response than the case when the metallic material is used. ABS resins or the like having a relatively high density show good characteristics in comparison with Teflon resin or the like, but, in comparison with metals such as aluminum, have meaningfully inferior thermal conductivity. Also, when the resin is used to form the heat conduction unit, it is preferable to take account of the heating temperature required in the operation of gene detection and use materials showing sufficient thermal resistance at that heating temperature even when used repeatedly.

Figure 3:
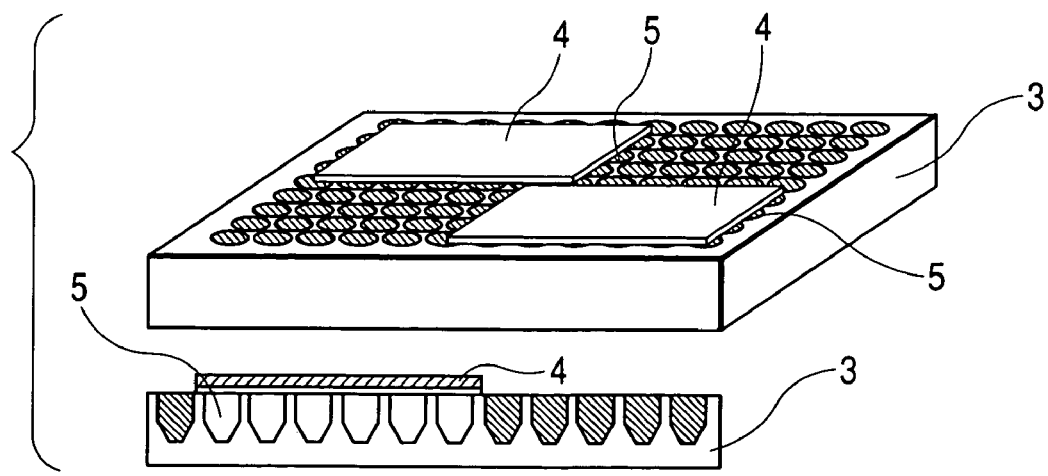
FIG. 3 is a diagrammatic illustration of an embodiment in which a heat-conductive material as a heat conduction means has been set to a temperature control means (heat block) in the temperature control system according to the present invention.

A further example shown in FIG. 3 is an example in which a gummy heat conduction means 5 is used. In this example, any member having the sandwiching bond face 1 like that shown in FIG. 1 or 2 is not used. The gummy heat conduction means 5 shown in this example is brought into close contact with the back of the substrate of a genetic chip 4 between the genetic chip 4 and the temperature control means 3 serving as a heating means or cooling means, by its pressing into a plurality of holes the latter has. This heat conduction means 5 is used to effect heat conduction in a good efficiency. The temperature control means 3 serving as a heating means or cooling means, shown in FIG. 3, is exemplified as a means of a heat block type intended for microtubes or the like. In this example, when the temperature control means 3 serving as a heating means or cooling means is used, which is of a form that microtubes or the like are inserted to the holes to effect heat conduction through wall surfaces, the holes are filled with the gummy temperature control means 5 by its pressing to the interiors of the holes. This brings an improvement in heat conduction efficiency.

The gummy temperature control means 5 (heat-conductive material) may preferably have an appropriate flowability. However, materials which may greatly change in its flowability with heating or cooling is not preferable in many cases because there is a high possibility that the heat conduction efficiency also changes. In general, in the operation of gene detection, the temperature of the genetic chip is set within the approximate range from a few ° C. to 95° C. Hence, it is preferable to select materials capable of maintain their flowability and plasticity within this temperature range. As materials for the gummy temperature control means 5, it is desirable to select those satisfying the above requirement on flowability and at the same time having heat conduction efficiency as high as possible.

In FIGS. 1 to 3, forms are exemplified in which the heat conduction unit or other form, having the heat-conductive material as the heat conduction means, is sandwichedly bonded to the whole back of the slide glass substrate of the genetic chip. Besides, the shape and position of the heat-conductive material (heat conduction means) to be used may be adjusted in accordance with the shape of an array where the probes have been immobilized.

Figure 4:
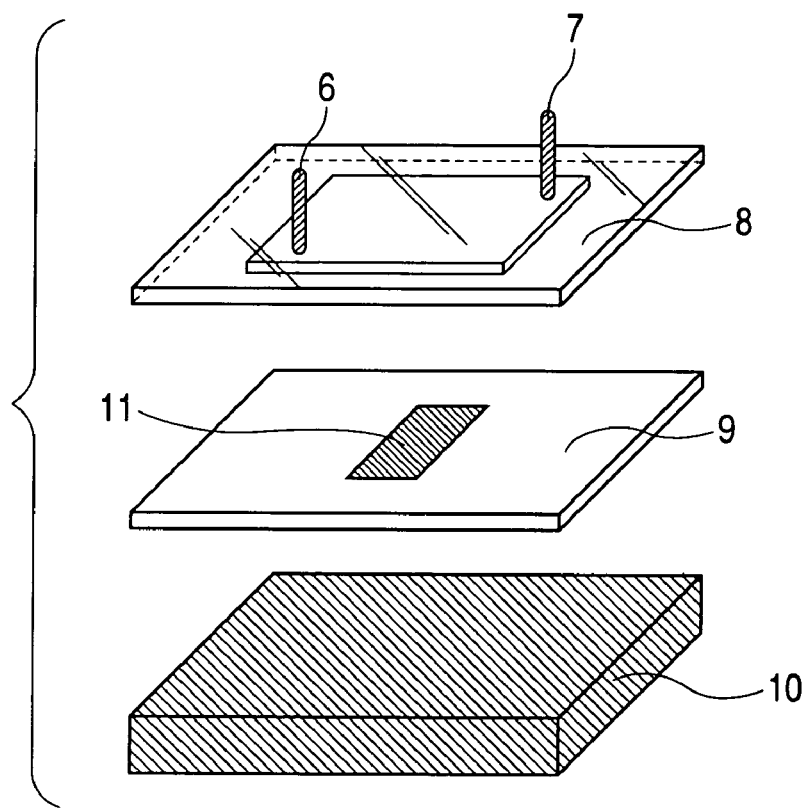
FIG. 4 is a diagrammatic illustration of an embodiment of the construction in which a genetic chip is to be set, in the temperature control system according to the present invention.
Figure 5:
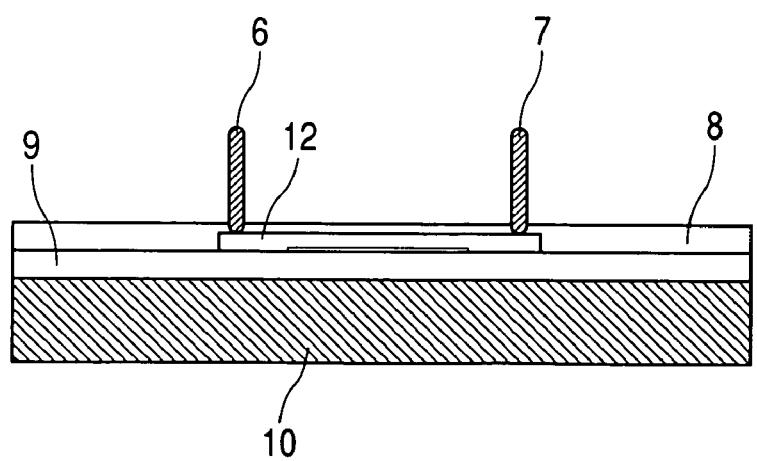
FIG. 5 is a diagrammatic illustration of an embodiment of the state in which a genetic chip has been set, in the temperature control system according to the present invention.

FIG. 4 is a diagrammatic illustration of an embodiment of the construction in which the genetic chip is to be set, according to the present invention. FIG. 5 shows the state in which the genetic chip has been set.

In FIGS. 4 and 5, reference numeral 6 denotes a fluid feed inlet; 7, a fluid discharge outlet; 8, a fluid supply cover; 9, a genetic chip; 10, a heat conduction unit (platelike; different in shape from those shown in FIGS. 1 and 2). Reference numeral 11 in FIG. 4 denotes a probe-immobilized face illustrated diagrammatically. Reference numeral 12 in FIG. 5 denotes a space formed partly between the fluid supply cover 8 and the genetic chip 9 in the state they have been laminated to each other; the space being formed by a recess provided in the fluid supply cover 8. The heat conduction unit 10 fitted to the genetic chip may be disposed in close contact with a heating means or the like such as a temperature-adjustable hot plate to enable adjustment of temperature of the probe-formed face 11. A specimen solution is fed into the space 12 through the fluid feed inlet 6, and the hybridization reaction is effected in the state the temperature of the probe-formed face 11 has been kept from scattering. Thus, analysis can be made in a good precision.

In another embodiment, the heat conduction means may be provided on the wall surfaces constituting the space so that the temperature of the probe-formed face can be adjusted.

EXAMPLES

The present invention is described below in greater detail by giving Examples. Incidentally, although these Examples demonstrate examples of best-mode embodiments according to the present invention, the present invention is by no means limited to the forms in these Examples.

Example 1

Production of DNA Probe Arrays (1) Cleaning of Glass Substrate:
A glass substrate made of synthesized quartz (size: 25 mm×75 mm×1 mm; available from Iiyama Tokushu Garasu K.K.) was set in a heat-resistant and alkali-resistant rack, and these were immersed in a cleaning fluid for ultrasonic cleaning, having been prepared in a stated concentration. These were immersed in the cleaning fluid overnight, and thereafter subjected to ultrasonic cleaning for 20 minutes. Subsequently, the substrate was taken out, and then rinsed lightly with pure water, followed by ultrasonic cleaning for 20 minutes in ultra-pure water. Next, the substrate was immersed for 10 minutes in an aqueous 1N sodium hydroxide solution heated to 80° C. The cleaning with pure water and the cleaning with ultra-pure water were again carried out to prepare a cleaned quartz glass substrate for a DNA chip.

(2) Surface Treatment:

An aminosilane coupling agent KBM-603 (available from Shin-Etsu Silicone Co., Ltd.) was so dissolved in pure water as to be in a concentration of 1% by weight, followed by stirring at room temperature for 2 hours. Subsequently the cleaned glass substrate was immersed in the aqueous aminosilane coupling agent solution thus formed, and was left at room temperature for 20 minutes. The glass substrate was drawn up, and then the substrate surface was lightly washed with pure water. Thereafter, nitrogen gas was blown on the substrate on its both sides to dry it. Next, the substrate thus dried was baked for 1 hour in an oven heated to 120° C., to complete the coupling-agent treatment of the surface. With this aminosilane coupling-agent treatment, amino groups are introduced to the substrate surface.

Meanwhile, in a 1:1 (volume ratio) mixed solvent of dimethyl sulfoxide and ethanol, N-(6-maleimidocaproyloxy)succinimide (hereinafter abbreviated as EMCS) was so dissolved as to be in a final concentration of 0.3 mg/ml to prepare an EMCS solution. After the baking was completed, the glass substrate was cooled, and then immersed at a room temperature for 2 hours in the EMCS solution thus prepared. This treatment makes the amino groups introduced to the substrate surface react with the succinimide groups of EMCS, so that maleimide groups derived from EMCS are introduced to the substrate surface. The glass substrate drawn up from the EMCS solution was washed with the above mixed solvent of dimethyl sulfoxide and ethanol. This substrate surface was further washed with ethanol, and thereafter the glass substrate thus surface-treated was dried in an atmosphere of nitrogen gas.

(3) Synthesis of Probe DNA:

Three kinds of 18-mer probe DNA having the following base sequences (SEQ ID NO: 1 to 3) were prepared and then modified with a sulfanyl group at the 5' terminal by conventional procedure to synthesize DNA oligomers of the following Formulas 1 to 3.

```
ACTGGCCGTCGTTTTACA   (SEQ ID NO:1)

ACTGGCCATCGTTTTACA   (SEQ ID NO:2)

ACTGGCAATCGTTTTACA   (SEQ ID NO:3)

5' HS-(CH2)6-O-PO2-O-ACTGGCCGTCGTTTTACA 3'   (Formula 1)

5' HS-(CH2)6-O-PO2-O-ACTGGCCATCGTTTTACA 3'   (Formula 2)

5' HS-(CH2)6-O-PO2-O-ACTGGCAATCGTTTTACA 3'   (Formula 3)
```

After their syntheses, these DNA oligomers were purified by high-speed liquid chromatography, and thereafter desalted and dried so as to be used in the following experiments.

(4) Ejection of DNA Probes by BJ Printer and Binding to Substrate:

An aqueous solution containing 7.5% by weight of glycerol, 7.5% by weight of thiodiglycerol, 7.5% by weight of urea and 1.0% by weight of ACETYLENOL EH (Kawaken Fine Chemicals Co., Ltd.) was beforehand prepared. Subsequently, the single-stranded DNA of each Sequence Number (SEQ ID NO: 1, 2 or 3) thus synthesized was so dissolved in the above aqueous solution as to be in a final concentration of 50 micrograms/ml. The DNA solution thus obtained was filled into an ink tank for a bubble jet printer (trade name: BJF-850; manufactured by CANON INC.), which was then fitted to the printing head.

The bubble jet printer used here is a printer remodeled so that it can perform printing on flat plates. This bubble jet printer can also shoot ink dots in a corresponding pattern by inputting a print pattern according to a stated file preparation method, and can perform spotting about 5 picoliters of the DNA solution at about 120 micrometer pitches.

Subsequently, using this remodeled bubble jet printer, the probes of Sequence Numbers 1 to 3 were each spotted on one surface-treated glass substrate over 144 spots in total, in a matrix of 12 spots in column and 4 spots in row. After making sure that the intended spot printing was performed, this glass substrate was left for 30 minutes in a moistening chamber to allow the maleimide groups on the glass substrate surface to react with the sulfanyl group at the 5' terminals of DNA probes.

(5) Washing:

After the reaction carried out for 30 minutes, the DNA solution remaining on the surfaces was washed away with a 10 mM phosphate buffer solution (pH 7.0) containing 100 mM of NaCl to obtain genetic chips to each glass substrate surface of which each single-stranded DNA spotted in a matrix was immobilized (DNA probe array substrates).

—Production of Heat Conduction Unit Made of Aluminum—

A heat conduction unit having the shape shown in FIG. 1 was produced by cutting from an aluminum block. The heat conduction unit thus produced was in a size that the sandwiching bond face to the genetic chip was 27 mm×85 mm×1.5 mm in dimensions and the legs were in a cylindrical shape of 10 mm in diameter and 25 mm in length. The legs were provided at a fitting pitch of 16 mm, and four legs in total were set on the back side of the sandwiching bond face. At four corners of the sandwiching bond face, holes to receive bolts (threaded holes) for fastening a fluid supply cover described below were provided.

—Production of Fluid Supply Cover—

A fluid supply cover like that denoted by reference numeral 8 in FIG. 4 or 5, used to supply the specimen solution and washing fluid to the probe-immobilized face at the genetic chip surface, was produced using an acrylic resin. In order to keep the stated space between the probe-immobilized face and the inner surface of the fluid supply cover, a space of 0.5 mm in thickness was provided, and the space thus formed was made to serve as a fluid chamber. The point of contact between the fluid supply cover and the probe-immobilized face of the genetic chip was sealed with a silicone rubber packing. A fluid feed inlet and a discharge outlet of 1 mm in inner diameter each were provided on the outside of the fluid supply cover. To fasten the fluid supply cover, holes through which fastening bolts were to be passed were provided at four corners of the fluid supply cover so that these holes were fittable to the above threaded holes having been provided at the four corners of the sandwiching bond face of the heat conduction unit, so as to be bolted with fixing bolts.

To the fluid feed inlet on the outside, as shown in FIG. 4 or 5, a silicone rubber tube 6 was connected, and this was set to a tube pump. A silicone rubber tube 7 was also connected to the discharge outlet, and then connected to a waste liquor bottle.

—Fitting of Genetic Chips—

Each genetic chip, the heat conduction unit and the fluid supply cover were set up by the procedure described below.

First, the sandwiching bond face of the heat conduction unit, to which the genetic chip is to be bonded, was thinly coated with a heat-resistant silicone grease, and thereafter the back of the genetic chip was contact-bonded thereto. When contact-bonded, it was minded that any air bubbles should not enter the grease in order to enhance the adhesion between the heat conduction unit and the back of the genetic chip. Subsequently, the fluid supply cover was so put on the surface side of the genetic chip as to cover the probe-immobilized face, and then, paying attention to uniform the load applied by the four fixing bolts, bolted to the heat conduction unit to fasten the fluid supply cover thereto sandwiching the genetic chip between them.

The resulting assemblage of each genetic chip, heat conduction unit and fluid supply cover was set on a heat block device (CHT-100; manufactured by Iwaki Glass Company Limited). The heat block of the device used is an aluminum block for 1.5 to 2.0 ml of microtubes.

—Preparation of Model Specimen for Inspection—

A model specimen used to inspect the function of the above temperature control mechanism was prepared in the following way. As a model target nucleic acid (gene), single-stranded nucleic acid fragments having a complementary base sequence in respect to the single-stranded nucleic acid fragments of Sequence Number 1 were synthesized, and a fluorescent dye (rhodamine) was labeled to the 5' terminal by conventional procedure. Using the model target nucleic acid thus synthesized, a composition (model specimen) shown below was prepared.

TABLE 1

(Model Specimen Composition)

| Components | Concentration |
|---|---|
| Model target nucleic acid | 10 nM |
| Herring spermatozoon DNA (having been ultrasonic-crushed) | corr. to 1 µM (as 200 bp on average) |
| NaCl | 100 mM |
| pH 7 Phosphate buffer solution | 10 mM |
| Formamide | 10% (v/v) |

—Blocking/Hybridization—

After assemblage, first a blocking fluid was fed to each genetic chip set to the heat block device, by means of a tube pump to fill the fluid chamber with the solution. As the blocking fluid, used was one prepared by dissolving bovine serum albumin (BSA) in physiological saline (PBS) in a concentration of 2% (w/w). After the space (fluid chamber) between the probe-immobilized face of the genetic chip and the fluid supply cover was filled with the fluid, the tube pump was stopped, and the discharge outlet side was also closed with a pinch cock. After brought into such a closed state, the system was left at room temperature for 2 hours.

After it was left for 2 hours, the heat block was preheated to 55° C., and thereafter the pinch cock of the discharge outlet was opened, and the model specimen fluid was supplied through the fluid feed inlet by means of the tube pump to displace and fill the inside of the fluid chamber with the model specimen. Here, the model specimen fluid was beforehand subjected to heat denaturation treatment at 95° C. for 3 minutes and quenching treatment, immediately before it was supplied to the genetic chip. After the space (fluid chamber) between the probe-immobilized face of the genetic chip and the fluid supply cover was filled with the model specimen fluid, the tube pump was stopped, and the discharge outlet side was also closed with a pinch cock. Keeping this closed state, and temperature-controlling the heat block at 55° C., the system was left for 16 hours.

—Washing—

After the system was left for 16 hours under the temperature control, the pinch cock of the discharge outlet was opened, and a washing fluid 1 shown below was supplied through the fluid feed inlet by means of the tube pump to wash the genetic chip. The washing fluid 1 was supplied at a supply rate of 1 ml/minute, during which, as the temperature of the heat block was kept at 55° C., the washing was carried out for 10 minutes.

TABLE 2

(Washing Fluid 1 Composition)

| Components | Concentration |
|---|---|
| NaCl | 100 mM |
| pH 7 Phosphate buffer solution | 10 mM |
| Sodium dodecylsulfate | 0.1% (w/w) |

Next, the supply of the washing fluid 1 was stopped, and the temperature of the heat block was changed to 25° C. The washing fluid 1 was changed for a washing fluid 2 shown below. After making sure that the temperature became stable at 25° C., the washing fluid 2 was supplied at a supply rate of 1 ml/minute to start the washing again. The washing was carried out for 3 minutes.

TABLE 3

(Washing Fluid 2 Composition)

| Components | Concentration |
|---|---|
| NaCl | 1.8 g/L |
| Sodium citrate dihydrate | 0.9 g/L |
| Aqueous NaOH solution | appropriate (adjusted to pH 7) |

—Drying—

After the washing was completed, each genetic chip having been set up was detached from the heat block device. The heat conduction unit and the fluid supply cover were also detached to take out the genetic chip, which was in the state of slide glass. The genetic chip taken out was dried by blowing nitrogen gas thereon.

—Fluorometry—

Each genetic chip thus dried was set in an array scanner GENEPIX 400B (manufactured by Axon Co.) to carry out fluorometry by conventional procedure for each spot in the matrix-form DNA array. Stated specifically, using a laser of 532 nm in wavelength, the probe-immobilized face of the genetic chip was scanned to measure the fluorescence of the rhodamine labeling the model target nucleic acid.

The fluorometry was carried out using an analyzing software (GENEPIX PRO 3.0) attached to the array scanner. The amount of fluorescence was measured at a scan resolution of 5 microns, and the spot was detected in automatic alignment. Comparison was made by the total sum of brightness (fluorescent brightness) of 32 pixels at the center of the spot detected.

—Results of Fluorometry—

Assuming as 100 the average fluorescent brightness of the DNA probe spots of Sequence Number 1, the DNA probe spots of Sequence Number 2 and the DNA probe spots of Sequence Number 3 showed a fluorescent brightness of 40 and 8, respectively. Also, its scattering in 48 spots in total of the DNA probe spots of Sequence Number 1 was 109% of the average value as maximum value, and 93% of the average value as minimum value. The scattering in 48 spots in total of the DNA probe spots of Sequence Number 2 was 111% of the average value as maximum value, and 90% of the average value as minimum value. The scattering in 48 spots in total of the DNA probe spots of Sequence Number 3 was 108% of the average value as maximum value, and 89% of the average value as minimum value.

Comparative Example 1

Genetic chips making use of quartz glass substrates were produced in the same manner as in Example 1. Using each genetic chip produced, the detection was operated using a hybridizing cassette and an oven, commercially available. What differed from Example 1 were as follows:

The heat conduction unit and the fluid supply cover were not used, and the probe-immobilized face was covered with a commercially available cover glass by conventional procedure, and hybridization making use of the hybridizing cassette was carried out. The temperature during the hybridization reaction was controlled by means of an oven. In the washing thereafter, the washing fluid was temperature-controlled using a water bath.

—Results of Fluorometry—

The fluorescent brightness in virtue of labeling was measured by the same method and procedure as those in Example 1.

Assuming as 100 the average fluorescent brightness of the DNA probe spots of Sequence Number 1, the DNA probe spots of Sequence Number 2 and the DNA probe spots of Sequence Number 3 showed a fluorescent brightness of 65 and 34, respectively. Also, its scattering in 48 spots in total of the DNA probe spots of Sequence Number 1 was 121% of the average value as maximum value, and 82% of the average value as minimum value. The scattering in 48 spots in total of the DNA probe spots of Sequence Number 2 was 144% of the average value as maximum value, and 56% of the average value as minimum value. The scattering in 48 spots in total of the DNA probe spots of Sequence Number 3 was 137% of the average value as maximum value, and 52% of the average value as minimum value.

Example 2

Production of Genetic Chips

Produced in the same manner as in Example 1.

—Production of Heat Conduction Unit Made of Aluminum—

A heat conduction unit having the shape shown in FIG. 2 was produced by cutting from an aluminum block. The heat conduction unit thus produced was in a size that the sandwiching bond face to the genetic chip was 27 mm×85 mm×1.5 mm in dimensions and the legs were in a conical frustum shape of 6 mm in diameter at the base, 3 mm in diameter at the end and 11 mm in total height. The legs were provided at a fitting pitch of 9 mm, and 8 legs×3 lines=24 legs in total were set on the back side of the sandwiching bond face. At four corners of the sandwiching bond face, holes to receive bolts (threaded holes) for fastening a fluid supply cover described below were provided.

—Production of Fluid Supply Cover—

The same one as that in Example 1 was produced and used.

—Fitting of Genetic Chips—

Each genetic chip, the heat conduction unit and the fluid supply cover were set up in the same manner as in Example 1.

The resulting assemblage of each genetic chip, heat conduction unit and fluid supply cover was set on a heat block of a PCR device (PCT-100, manufactured by MJ Research Co.).

—Preparation of Model Specimen—

A model specimen was prepared in the same manner as in Example 1.

—Blocking/Hybridization, Washing & Drying—

Carried out under the same conditions as those in Example 1.

—Fluorometry & Results of Analyses—

The fluorescent brightness in virtue of labeling was measured by the same method and procedure as those in Example 1.

Assuming as 100 the average fluorescent brightness of the DNA probe spots of Sequence Number 1, the DNA probe spots of Sequence Number 2 and the DNA probe spots of Sequence Number 3 showed a fluorescent brightness of 42 and 11, respectively. Also, its scattering in 48 spots in total of the DNA probe spots of Sequence Number 1 was 107% of the average value as maximum value, and 94% of the average value as minimum value. The scattering in 48 spots in total of the DNA probe spots of Sequence Number 2 was 110% of the average value as maximum value, and 93% of the average value as minimum value. The scattering in 48 spots in total of the DNA probe spots of Sequence Number 3 was 112% of the average value as maximum value, and 91% of the average value as minimum value.

Example 3

Production of Genetic Chips

Produced in the same manner as in Example 1.

—Production of Fluid Supply Cover—

The same one as that in Example 1 was produced and used.

—Production of Backing Unit Plate Made of Aluminum & Preparation of Heat-conductive Material—

As a backing unit plate made of aluminum (hereinafter "backing aluminum plate"), an aluminum plate of 1.5 mm in thickness was cut out in a size of 27 mm in width and 85 mm in length. At four corners of this plate, holes to receive bolts (threaded holes) for fastening the fluid supply cover were provided. Separately, for use as the heat-conductive material, powdery copper was added to a silicone resin caulking material in a concentration of 80% (w/w), and these were quickly kneaded so as to come uniform, to prepare a heat-conductive caulking material.

—Fitting of Genetic Chips—

Each genetic chip, the fluid supply cover and the backing aluminum plate for fastening the fluid supply cover were set up by the procedure described below.

First, the top surface of the backing aluminum plate was thinly coated with a heat-resistant silicone grease, and thereafter the back of the genetic chip was contact-bonded thereto. When contact-bonded, it was minded that any air bubbles should not enter the grease in order to enhance the adhesion between the backing aluminum plate and the back of the genetic chip. Subsequently, the fluid supply cover was so put on the surface side of the genetic chip as to cover the probe-immobilized face, and then, paying attention to uniform the load applied by the four fixing bolts, bolted to the backing aluminum plate to fasten the fluid supply cover thereto sandwiching the genetic chip between them.

An appropriate amount of the heat-conductive caulking material mixed with copper powder was put on a heat block of a PCR device (PCT-100, manufactured by MJ Research Co.), and was set thereto by spreading it with a dummy backing aluminum plate to a necessary size. On this caulking material mixed with copper powder, thus spread, the assemblage of each genetic chip, fluid supply cover and backing aluminum plate was so contact-bonded that the backing aluminum plate came into close contact with the caulking material. Thus, the fitting was completed.

—Preparation of Model Specimen—

A model specimen was prepared in the same manner as in Example 1.

—Blocking/Hybridization, Washing & Drying—

Carried out under the same conditions as those in Example 1.

—Fluorometry & Results of Analyses—

The fluorescent brightness in virtue of labeling was measured by the same method and procedure as those in Example 1.

Assuming as 100 the average fluorescent brightness of the DNA probe spots of Sequence Number 1, the DNA probe spots of Sequence Number 2 and the DNA probe spots of Sequence Number 3 showed a fluorescent brightness of 39 and 9, respectively. Also, its scattering in 48 spots in total of the DNA probe spots of Sequence Number 1 was 105% of the average value as maximum value, and 91% of the average value as minimum value. The scattering in 48 spots in total of the DNA probe spots of Sequence Number 2 was 109% of the average value as maximum value, and 95% of the average value as minimum value. The scattering in 48 spots in total of the DNA probe spots of Sequence Number 3 was 111% of the average value as maximum value, and 90% of the average value as minimum value.

Example 4

Production of Genetic Chips

Produced in the same manner as in Example 1.

—Production of Fluid Supply Cover—

Basically the same one as that in Example 1 was produced and used, except that flexible tubes (silicone tubes of 1 mm each in inner diameter) were connected to the fluid feed inlet and discharge outlet.

—Production of Backing Unit Plate Made of Aluminum & Preparation of Heat-conductive Material—

As a backing unit plate made of aluminum (backing aluminum plate), an aluminum plate of 1.5 mm in thickness was cut out in a size of 27 mm in width and 85 mm in length. At four corners of this plate, holes to receive bolts (threaded holes) for fastening the fluid supply cover were provided. Separately, for use as the heat-conductive material, powdery copper was added to a silicone resin caulking material in a concentration of 80% (w/w), and these were quickly kneaded so as to come uniform, to prepare a heat-conductive caulking material.

—Fitting of Genetic Chips—

Each genetic chip, the fluid supply cover and the backing aluminum plate were set up in the same manner as in Example 3.

An appropriate amount of the heat-conductive caulking material mixed with copper powder was put on a heat block of a PCR device (PCT-100, manufactured by MJ Research Co.), and was set thereto by spreading it with a dummy backing aluminum plate to a necessary size. On this caulking material mixed with copper powder, thus spread, the assemblage of each genetic chip, fluid supply cover and backing aluminum plate was so contact-bonded that the top surface of the fluid supply cover came into close contact with the caulking material, i.e., in the state the genetic chip having the fluid supply cover on its surface side and the backing aluminum plate on its back side was put upside down.

Thus, the fitting was completed. Here, it was minded that the flexible tubes connected to the fluid feed inlet and discharge outlet should not hinder the adhesion between the caulking material and the fluid supply cover and also the fluid supply should not be obstructed because of their bending or the like.

—Preparation of Model Specimen—

A model specimen was prepared in the same manner as in Example 1.

—Blocking/Hybridization, Washing & Drying—

Carried out under the same conditions as those in Example 1.

—Fluorometry & Results of Analyses—

The fluorescent brightness in virtue of labeling was measured by the same method and procedure as those in Example 1.

Assuming as 100 the average fluorescent brightness of the DNA probe spots of Sequence Number 1, the DNA probe spots of Sequence Number 2 and the DNA probe spots of Sequence Number 3 showed a fluorescent brightness of 37 and 10, respectively. Also, its scattering in 48 spots in total of the DNA probe spots of Sequence Number 1 was 108% of the average value as maximum value, and 92% of the average value as minimum value. The scattering in 48 spots in total of the DNA probe spots of Sequence Number 2 was 111% of the average value as maximum value, and 94% of the average value as minimum value. The scattering in 48 spots in total of the DNA probe spots of Sequence Number 3 was 110% of the average value as maximum value, and 92% of the average value as minimum value.

In the foregoing, preferred embodiments of the present invention have been described in detail. The present invention is by no means limited to what have been constructed as described above. The present invention may preferably be applied to genetic chips for detecting target genes by hybridization. Without limitation thereto, the present invention is also applicable to a probe substrate to the substrate surface of which, as probe molecules, those bindable specifically to a target substance have been immobilized.

As examples of such probe molecules, including the above embodiments, any of DNA, RNA, cDNA (complementary DNA), PNA, oligonucleotides, polynucleotides, other nucleic acids, oligopeptides, polypeptides, proteins, enzymes, substrates to enzymes, antibodies, epitopes against antibodies, antigens, hormones, hormone receptors, ligands, ligand receptors, oligosaccharides and polysaccharides may be used. Two or more of any of these may optionally be used in combination.

What is claimed is:

1. A system for reaction of a nucleic acid comprising:
   a reaction unit comprising:
   a nucleic acid probe array substrate having nucleic acid probes immobilized in an array on a surface of the substrate:
   a cover member for forming a chamber with said probes immobilized on said surface, wherein a liquid can be filled into the chamber so as to apply said liquid to each of said probes;
   a heat conduction member for improving thermal diffusion in the liquid within said chamber, the heat conduction member being in contact with said substrate or said cover member with their contacting surfaces being flat and having no recesses; and
   a temperature control block for controlling the temperature of said heat conduction member,
   wherein said temperature control block includes a plurality of holes at a contact portion for inserting microtubes thereinto, and
   wherein said heat conduction member being for filling the plurality of holes at the contact portion of said temperature control block including a plurality of legs and each of the plurality of legs of said heat conduction member is adapted to be inserted into and in close contact with each one of the plurality of holes at the contact portion of said temperature control block, which is located on a back surface of said substrate, and the temperature control block being in contact with said substrate or said cover member.

2. A system for reaction of a nucleic acid according to claim 1, wherein said temperature control block is a heat block adapted to receive a microtube.

3. The system according to claim 2, wherein said heat conduction member is formed of metal, resin or a composite of metal and resin.

4. A reaction unit for use in the system for reaction according to claim 1.

5. A heat conduction adapter for using a heater with a plurality of holes for microtubes in temperature control for a nucleic acid probe array substrate, the heat conduction adapter comprising:
   a face provided with a plurality of legs having the same shape as that of the microtubes, and another face being flat and having no recesses for contacting with a face of the nucleic acid probe array substrate or a cover forming a chamber with the nucleic acid probe array substrate, wherein the plurality of legs on the face of the heat conduction adapter are fitted into the plurality of holes of the heat conduction adapter, thus bringing the heater into thermal contact with the nucleic acid probe array.

6. A method for detecting genes by utilizing as a detection means a substrate to the substrate surface of which a plurality of nucleic-acid probes containing single-stranded nucleic acid fragments having a complementary sequence in respect to a target DNA have been immobilized in order that the target DNA contained in a specimen is detected according to hybridization; the method comprising:

providing the heat conduction adaptor of claim 5;

disposing said heat conduction adaptor on the back of the substrate to the substrate surface of which the plurality of single-stranded nucleic acid fragments have been immobilized, and in contact with the back of the substrate;

disposing a heater or a cooler in contact with said heat conduction adaptor;

providing a temperature controller for controlling the amount of heat flowing across the heater or cooler and said heat conduction adaptor to control the temperature of the heat-conductive material;

providing a specimen comprising the target DNA to the substrate surface comprising the immobilizing nucleic acid fragments;

performing a hybridization reaction; and detecting the hybridization, the detecting being operated while the substrate standing bonded sandwichedly and the specimen standing in contact with the substrate surface are temperature-controlled through the temperature control of the heat-conductive material by the temperature controller during the operation of gene detection.

7. The method according to claim 6, wherein, in a plurality of steps involved in the gene detection, said substrate and said specimen standing in contact with the substrate surface are temperature-controlled; and the temperature in the plurality of steps requiring temperature control is successively controlled by the temperature controller which utilizes said heater.

8. The method according to claim 6, wherein, in a plurality of steps involved in the gene detection, said substrate and said specimen standing in contact with the substrate surface are temperature-controlled; and the temperature in the plurality of steps requiring temperature control is successively controlled by the temperature controller which utilizes said cooler.

9. The method according to claim 6, wherein, as said heat-conductive material, which is utilized for the temperature control the substrate and of the specimen standing in contact with the substrate surface, a heat-conductive material is used which is formed of any one of a metal and a resin or a composite of these two or more.

10. A method for detecting genes by utilizing as a detector a substrate to the substrate surface of which a plurality of nucleic-acid probes containing single-stranded nucleic acid fragments having a complementary sequence in respect to a target DNA have been immobilized in order that the target DNA contained in a specimen is detected according to hybridization; the method comprising:

providing the heat conduction adaptor of claim 5;

disposing said heat conduction adaptor on the surface of the substrate to the substrate surface of which the plurality of single-stranded nucleic acid fragments have been immobilized, facing, and in contact with, the substrate surface, partly leaving a space for feeding the specimen thereinto;

disposing a heater or a cooler in contact with said heat conduction adaptor;

providing a temperature controller for controlling the amount of heat flowing across the heating means or cooling means and said heat conduction adaptor to control the temperature of the heat-conductive material;

providing a specimen comprising the target DNA to the substrate surface comprising the immobilizing nucleic acid fragments;

performing a hybridization reaction; and detecting the hybridization, the detecting being operated while the specimen fed into the space and the substrate surface, which are in contact with the heat-conductive material, being temperature-controlled through the temperature control of said heat conduction adaptor by the temperature controller during the gene detection.

11. The method according to claim 10, wherein, in a plurality of steps involved in the gene detection, said substrate and said specimen standing in contact with the substrate surface are temperature-controlled; and the temperature in the plurality of steps requiring temperature control is successively controlled by the temperature controller which utilizes said heater.

12. The method according to claim 10, wherein, in a plurality of steps involved in the gene detection, said substrate and said specimen standing in contact with the substrate surface are temperature-controlled; and the temperature in the plurality of steps requiring temperature control is successively controlled by the temperature controller which utilizes said cooler.

13. The method according to claim 10, wherein, as said heat-conductive material, which is utilized for the temperature of the substrate and the specimen standing in contact with the substrate surface, said heat conduction adaptor is used which is formed of any one of a metal and a resin or a composite of these two or more.

* * * * *